(12) United States Patent
Che et al.

(10) Patent No.: US 9,831,449 B2
(45) Date of Patent: Nov. 28, 2017

(54) LIGHT-EMITTING MATERIALS FOR LIGHT-EMITTING DIODES

(71) Applicant: GUANGDONG AGLAIA OPTOELECTRONIC MATERIALS CO., LTD., Foshan, Guangdong (CN)

(72) Inventors: Chiming Che, Foshan (CN); Lifei Cai, Foshan (CN)

(73) Assignee: GUANGDONG AGLAIA OPTOELECTRONIC MATERIALS CO., LTD., Foshan (CN)

( * ) Notice: Subject to any disclaimer, the term of this patent is extended or adjusted under 35 U.S.C. 154(b) by 0 days.

(21) Appl. No.: 15/325,701

(22) PCT Filed: Mar. 16, 2015

(86) PCT No.: PCT/CN2015/074265
§ 371 (c)(1),
(2) Date: Jan. 11, 2017

(87) PCT Pub. No.: WO2016/004772
PCT Pub. Date: Jan. 14, 2016

(65) Prior Publication Data
US 2017/0162803 A1    Jun. 8, 2017

(30) Foreign Application Priority Data
Jul. 11, 2014    (CN) .......................... 2014 1 0332281

(51) Int. Cl.
*H01L 51/00* (2006.01)
*H01L 51/50* (2006.01)
*H01L 51/56* (2006.01)

(52) U.S. Cl.
CPC ...... *H01L 51/0087* (2013.01); *H01L 51/0003* (2013.01); *H01L 51/0005* (2013.01); *H01L 51/5004* (2013.01); *H01L 51/5012* (2013.01); *H01L 51/5056* (2013.01); *H01L 51/5072* (2013.01); *H01L 51/56* (2013.01)

(58) Field of Classification Search
CPC .................................................. H01L 51/0087
USPC ......................................................... 544/64
See application file for complete search history.

(56) References Cited

U.S. PATENT DOCUMENTS

| | | | |
|---|---|---|---|
| 4,356,429 | A | 10/1982 | Tang |
| 8,877,353 | B2 | 11/2014 | Che et al. |
| 8,957,217 | B2 | 2/2015 | Che et al. |
| 9,472,769 | B2 | 10/2016 | Yagi et al. |
| 2003/0205707 | A1 | 6/2003 | Chi-Ming |
| 2010/0084967 | A1 | 4/2010 | Takeda |
| 2013/0082245 | A1 | 4/2013 | Kottas et al. |
| 2015/0084028 | A1 | 3/2015 | Nii et al. |

FOREIGN PATENT DOCUMENTS

| | | |
|---|---|---|
| CN | 1649886 A | 8/2005 |
| CN | 1777663 A | 5/2006 |
| CN | 101646745 A | 2/2010 |
| CN | 101646746 A | 2/2010 |
| CN | 102898476 A | 1/2013 |
| CN | 103097395 A | 5/2013 |
| CN | 103619859 A | 3/2014 |

OTHER PUBLICATIONS

Che et al., "Photophysical Properties and OLED Applications of Phosphorescent Platinum(II) Schiff Base Complexes", Chemistry—A European Journal, vol. 16, Issue 1, 2010, pp. 233-247.
Tang et al., "Organic electroluminescent diodes", Applied Physics Letters, vol. 52, Issue 12, Sep. 21, 1987, pp. 913-915.
Vezzu et al., "Highly Luminescent Tetradentate Bis-Cyclometalated Platinum Complexes: Design, Synthesis, Structure, Photophysics, and Electroluminescence Application", Inorganic Chemistry, vol. 49, Issue 11, 2010, pp. 5107-5119.
Yan et al., "High-efficiency orange and yellow organic light-emitting devices using platinum(II) complexes containing extended π-conjugated cyclometalated ligands as dopant materials", Applied Physics Letters, vol. 91, Issue 6, Aug. 8, 2007, pp. 063508-1-063508-3.
Zhou et al., "Efficient Red Electroluminescent Devices with Sterically Hindered Phosphorescent Platinum(II) Schiff Base Complexes and Iridium Complex Codopant", Chemistry—An Asian Journal, vol. 9, Issue 10, 2014, pp. 2984-2994.
Zhao et al., "A 3-dimensional spiro-functionalized platinum(II) complex to suppress intermolecular π-π and Pt•••Pt supramolecular interactions for a high-performance electrophosphorescent device", Chemical Communications, vol. 48, Issue 32, 2012, pp. 3854-3856.

*Primary Examiner* — Kahsay Habte
(74) *Attorney, Agent, or Firm* — Maschoff Brennan (57) ABSTRACT

The present invention relates to light-emitting materials for light-emitting diodes. The structure for the light-emitting materials is shown in Formula I. The platinum (II) complexes of the present invention show high emission quantum efficiency, good thermal stability and low quenching constant, thus can be used for producing red light OLED with high efficiency and low efficiency attenuation.

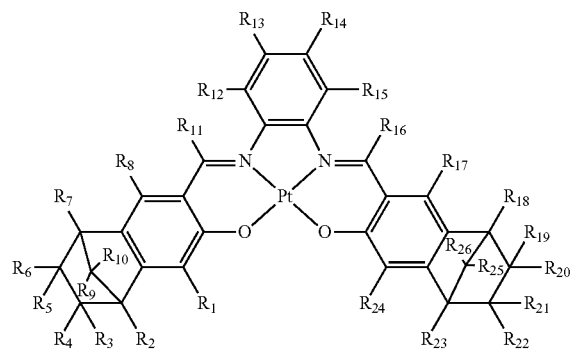

10 Claims, 3 Drawing Sheets

FIG. 1 i: weak base, platinum salt

LIGHT-EMITTING MATERIALS FOR LIGHT-EMITTING DIODES

TECHNICAL FIELD

The present invention relates to a light-emitting material, and in particular, to a novel platinum (II) complex light-emitting material and applications in organic light-emitting diodes (OLED) thereof.

BACKGROUND ART

In the 1980s, C. W. Tang disclosed a double-layer OLED (Organic Light-Emitting Device) (U.S. Pat. No. 4,356,429; Appl. Phys. Lett. 1987, 51, 12, 913). This finding is based on a multilayer structure comprising an emissive electron-transporting layer and a hole transport layer of appropriate organic material. $Alq_3$ (q: deprotonated 8-hydroxythionyl)) was used as emissive electron-transporting material. Since then, the material OLED used in continuous studies of OLED has the following advantages: (1) low operating voltage, (2) thin overall structure, (3) emitted light rather than modulated light, (4) good light-emitting efficiency, (5) panchromatic potential, and high contrast and resolution. These advantages suggest that OLEDs may be used in flat panel displays.

Organic small molecules are studied to improve the performance of OLEDs. Typically, phosphorescent materials are used as light emitters in the light-emitting layer of the OLED, but in different phosphorescent materials, complexes with iridium and platinum are still the dominant materials. Because the iridium-based material has octahedral geometry configuration, the OLED made by iridium-based material has high performance, in addition, it has no great efficiency attenuation. In contrast, platinum-based materials have a planar geometry, so OLEDs made from platinum-based materials have great efficiency attenuation although they have high performance; in other words, these devices can achieve high performance only under very low brightness, and at normal operating brightness levels, for example, below 1000 cd $m^{-2}$, the performance of devices will be lowered to a very low level. For example, we developed a class of platinum-containing phosphorescent materials in 2007 and devices made by such materials can achieve performance as high as 51.8 cd $A^{-1}$, but their performance drastically dropped to 50% of the highest performance (Appl. Phys. Lett. 91, 2007, 063508); therefore, only the iridium-based materials can be used in OLED products now.

In general, materials with high quenching constant (above $10^8$ $dm^3$ $mol^{-1}$ $s^{-1}$) may cause severe triplet and triplet annihilation cause rapid efficiency attenuation. In addition to efficiency attenuation, devices made by platinum-based materials can be operated in a very narrow doping window due to high quenching constant. In other words, devices with high efficiency and high color purity can only be achieved in a very small doping range (e.g. 1% to 2%), thus, platinum-based materials are not accepted in the industries.

In order to solve this problem, different researchers propose different schemes and prepare different materials. In 2010, we added a large group, Huo added a nonplanar base, and in 2012, Xie added a nonplanar base to a platinum-based material (Chem. Eur. J. 2010, 16, 233-247; Inorg. Chem. 2010, 49, 5107-5119; Chem. Commun. 2012, 48, 3854-3856). However, this problem has not been significantly improved, and the devices prepared still have over 50% efficiency attenuation, which demonstrated that the addition of large groups and non-planar groups are not usually a feasible solution to this problem.

SUMMARY OF THE INVENTION

In order to solve the above drawbacks, the present invention provides a novel platinum (II) complex light-emitting material having a low quenching constant, which are capable of manufacturing red-light OLEDs of high efficiency and low efficiency attenuation.

The present invention further provides a method for preparing a light-emitting material.

The present invention further provides a light-emitting device produced by the light-emitting material.

The structure of the light-emitting material for light-emitting diodes is shown as formula I, (I)

Wherein, $R_1$-$R_{26}$ are independently hydrogen, halogen, hydroxy, unsubstituted alkyl, substituted alkyl, cycloalkyl, unsubstituted aryl, substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl or alkoxycarbonyl, and $R_1$-$R_{26}$ can independently form a 5- to 8-membered ring with other adjacent R1-R26 groups.

Wherein, $R_1$-$R_{26}$ are independently hydrogen, halogen, hydroxy, C1-C6 alkyl, five- or six-membered cycloalkyl, five- or six-membered aryl, alkoxy, amino, nitro, cyano, and carboxyl, and $R_1$-$R_{26}$ may independently form a five- or six-membered ring with other adjacent $R_1$-$R_{26}$ groups.

Wherein, $R_{3-8}$ and $R_{17-22}$ are independently hydrogen.

Wherein, $R_1$, $R_{11}$, $R_{16}$, $R_{24}$ are independently hydrogen, $R_2$, $R_{23}$, $R_{9-10}$, $R_{25-26}$ are independently hydrogen, $C_1$-$C_6$ are alkyl.

Wherein, $R_{12-15}$ are independently hydrogen, halogen, hydroxy, $C_1$-$C_6$ alkyl, 5-membered or 6-membered cycloalkyl, 5-membered or 6-membered aryl, amino, nitro, cyano, or 5-membered or 6-membered aromatic rings formed by $R_{13}$ and $R_{14}$.

Wherein, $R_{13}$ and $R_{14}$ are independently hydrogen, halogen, $C_1$-$C_4$ alkyl, amino, nitro, cyano, or a benzene ring formed by R $R_{13}$ and $R_{14}$.

Wherein, $R_{12}$ and $R_{15}$ are independently hydrogen, $C_1$-$C_6$ alkyl.

The organic metal complex having the chemical structure of structure I is called a ring metallated complex, and the platinum center in structure I is +2 oxidation state and has a square planar geometrical shape. The coordination site of this platinum center is coordinated by a tetradentate ligand which is coordinated to the platinum center by two nitrogen donor bonds and two oxygen donor bonds. In order to meet the requirements of red light, the basic structure of the tetradentate ligand is Schiff base. As stated in the background art, the platinum complex with a Schiff base has a high quenching constant, and the devices prepared have high efficiency attenuation, which can not be improved even if large groups are added. In the present invention, the bicyclic ring attached to the phenol is a key part which can effectively reduce the low quenching constant. We can combine the two methods to obtain the effect that cannot be obtained with other groups through the structure I. In the invention, the center of the structure I (as indicated in bold line in the figure below) is the reason for that the material has a red light emission and has a low quenching constant:

Structure I

In structure I, other groups ($R_1$-$R_{26}$) do not seriously affect the luminescent properties and quenching constant of the materials, so they may be independently hydrogen, halogen, hydroxy, unsubstituted alkyl, substituted alkyl, cycloalkyl, unsubstituted aryl, substituted aryl, acyl, alkoxy, acyloxy, amino, nitro, acylamino, aralkyl, cyano, carboxy, thio, styryl, aminocarbonyl, carbamoyl, aryloxy, phenoxycarbonyl or alkoxycarbonyl. Each of $R_1$-$R_{26}$ may independently form a 5- to 8-membered ring with adjacent R groups.

For the purposes of this application, the terms halogen, alkyl, cycloalkyl, aryl, acyl, alkoxy and heterocyclic aromatic system or heterocyclic aromatic groups may have the following meanings, unless otherwise specified:

The halogen or halo as used herein includes fluorine, chlorine, bromine and iodine, preferably F, Cl, Br, particularly preferably F or Cl, most preferably F.

As used herein, aryl, aryl or aromatic systems include those having 6 to 30 carbon atoms, preferably 6 to 20 carbon atoms, more preferably 6 to 8 carbon atoms which are substituted by one aromatic ring or a plurality of fused aromatic rings. The appropriate aryl groups are, for example, phenyl, naphthyl, acenaphthenyl, acenaphthylenyl, anthryl, fluorenyl, phenalenyl. The aryl group may be unsubstituted (i.e., all the carbon atoms which may be substituted have hydrogen atom) or may be substituted at one, more than one, or all substitutable positions of the aryl. Appropriate substituents are, for example, halogen, preferably F, Br or Cl; alkyl, preferably alkyl having 1 to 20, 1 to 10 or 1 to 8 carbon atoms, particularly preferably methyl, ethyl, isopropyl or tertiary butyl; aryl group, preferred re-substituted or unsubstituted C6-aryl or fluorenyl; heteroaryl group, preferably a heteroaryl group containing at least one nitrogen atom, and particularly preferably a pyridyl group, the alkenyl group is a suitable substituent, preferably an alkenyl group having one double bond, particularly preferably al alkenyl having a double bond and 1 to 8 carbon atoms. Aryl groups, particularly preferred substituents selected from the group containing F and t-butyl, preferably a given aryl or a C6-aryl that can be optionally substituted by at least one of the foregoing substituents, C6-aryl is particularly preferably with 0, 1 or 2 forgoing substituents, $C_6$-aryl is particularly preferably an unsubstituted phenyl or substituted phenyl such as biphenyl, phenyl preferably substituted by two tert-butyl groups; for example, the aryl or aryl moiety as used herein is preferably phenyl, which may be unsubstituted or substituted with the above-described substituents, preferably substituted with halo, alkyl or aryl.

As used herein, alkyl or alkyl moieties include alkyl groups having 1 to 20 carbon atoms, preferably 1 to 10 carbon atoms, particularly from 1 to 6 carbon atoms. The alkyl group may be branched or straight chained and may be interrupted by one or more heteroatoms, preferably N, O or S. Also, the alkyl group may be substituted with one or more of the substituents mentioned for the aryl group. In addition, for alkyl groups, it is possible to have one or more aryl groups, all of the mentioned aryl groups are suitable for this purpose, and alkyl groups are particularly preferably selected from methyl, ethyl, iso-propyl, n-propyl, iso-butyl, n-butyl, t-butyl, sec-butyl, iso-pentyl, n-pentyl, sec-pentyl, neopentyl, n-hexyl, iso-hexyl and sec-hexyl, and particularly preferred tert-butyl, $C_4H_9$, $C_6H_{13}$.

As used herein, a cycloalkyl group is desirably cyclic alkyl groups, and preferred cycloalkyl groups containing 3 to 7 carbon atoms and including cyclopropyl, cyclopentyl, cyclohexyl, etc. Further, the cycloalkyl group may be optionally substituted with one or more substituents selected from halo, alkyl, t-butyl, C4H9, C6H13.

As used herein, an acyl group is a group that is connected to the CO group with a single bond, e.g. the alkyl used herein.

As used herein, an alkoxy group is an alkyl group that is connected to oxygen, e.g. the alkyl used herein.

As used herein, a heterocyclic aromatic system or a heterocyclic aromatic group is understood to be associated with an aromatic, $C_3$-$C_8$ cyclic group and including an oxygen or sulfur atom or 1-4 nitrogen atoms or an oxygen or a combination of an oxygen or a sulfur atom with at most two nitrogen atoms, and their substituents and benzo and pyrido-fused derivatives, for example, by linked via one of the ring-forming carbon atoms, the heterocyclic aromatic system heterocyclic aromatic group can be substituted by one or more of the substituents for the aryl group.

In some embodiments, the heteroaryl group may be a five- and six-membered-aromatic heterocyclic ring system carrying 0, 1, or 2 substituents which may be the same or different from each other. Typical examples of heteroaryl groups include, but are not limited to, unsubstituted furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, quinoline, isoquinoline, pyridazine, pyrimidine, purine and pyrazine, furan, 1,2,3-thiadiazole, 1,2,3-thiadiazole, 1,2,4-thiadiazole, triazole, benzotriazole, pteridine, benzoxazole, oxadiazole, benzopyrazole, quinolizine, cinnoline, phthalazine, quinazolyl and quinoxaline and mono- or di-substituted derivatives thereof. In some embodiments, the substituents are halo, hydroxy, cyano, O—C1-6-alkyl, C1-6-alkyl, hydroxy-C1-6-alkyl and amino-C1-6-alkyl.

Specific examples of platinum (II) complexes are shown below, but not limited to, the following complexes:

Complex 101

Complex 102

Complex 103

Complex 104

Complex 105

Complex 106

Complex 107

Complex 108

Complex 109

Complex 110

Complex 111

Complex 112

Complex 113

Complex 114

Complex 115

Complex 116

Complex 117

Complex 118

The OLED for thermal deposition and solution processing can be produced using the complexes with the structure I.

An organic light-emitting device containing one or more light-emitting materials for a light-emitting diode as described in claim 1.

Wherein, the light-emitting material for light-emitting diodes is applied in layers in the device by thermal deposition.

Wherein, the light-emitting material for light-emitting diodes is applied in layers in the device by spin coating.

Wherein, the light-emitting material for light-emitting diodes is applied in layers in the device by ink jet printing.

For the organic light emitting device described above, wherein the device emits a monochromatic-red color when an electric current is applied to the layer.

The platinum (II) complexes herein have high emission quantum efficiency, good thermal stability and low quenching constant, and they can be used to produce red light OLEDs with high efficiency and low efficiency attenuation.

DETAILED DESCRIPTIONS OF THE PREFERRED EMBODIMENTS

The following are embodiments of the preparation, physical properties, and electroluminescent data of platinum (II) complexes (light-emitting materials for light-emitting diodes). The embodiments are presented to help the understanding of the invention, which are not intended and should not be construed as limiting the invention as claimed in claims appended thereof in any way.

Unless otherwise indicated in the following embodiments, descriptions and claims, all parts and percentages are calculated by weight, and all temperatures are in degrees Celsius, and the pressure is the atmospheric pressure or close to atmospheric pressure.

All digitals, values and/or expressions of the ingredients, reaction conditions used in the descriptions and claims that are not used in embodiments or as otherwise indicated should be construed to be defined as "about" in all instances.

Any drawing or numerical range of a technical feature can be combined with drawings or parameters at different ranges with the same technical features, to form a numerical range.

Figure 1:
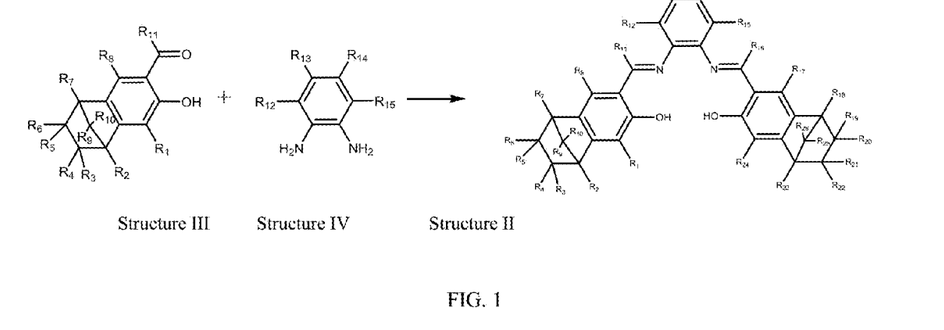
FIG. 1: a scheme for the synthesis of ligands having a chemical structure of Structure II.

Embodiment 201—General Method for Preparing a Ligand Having the Chemical Structure of Structure II Referring to FIG. 1, the chemical structure having structure II is obtained by condensation of two imine bonds with a chemical containing o-phenylenediamine group (structure III) and a chemical compound containing phenol and double rings (structure IV). (The above structures III and IV are commercially available).

Embodiment 202—Preparation of Ligand 301

Ligand 301

The ligand 301 is prepared by the method in Embodiment 201, wherein $R_1$-$R_{26}$ are hydrogen. Yield: 100%. $^1$H NMR (500 MHz, CDCl$_3$) δ 13.33 (s, 2H), 8.54 (s, 2H), 7.34-7.22 (m, 2H), 7.22-7.11 (m, 2H), 7.09 (s, 2H), 6.87 (s, 2H), 3.32 (d, J=11.0 Hz, 4H), 1.90 (d, J=7.5 Hz, 4H), 1.73 (d, J=8.1 Hz, 2H), 1.54 (d, J=8.6 Hz, 2H), 1.20 (d, J=5.7 Hz, 4H).

Figure 2:
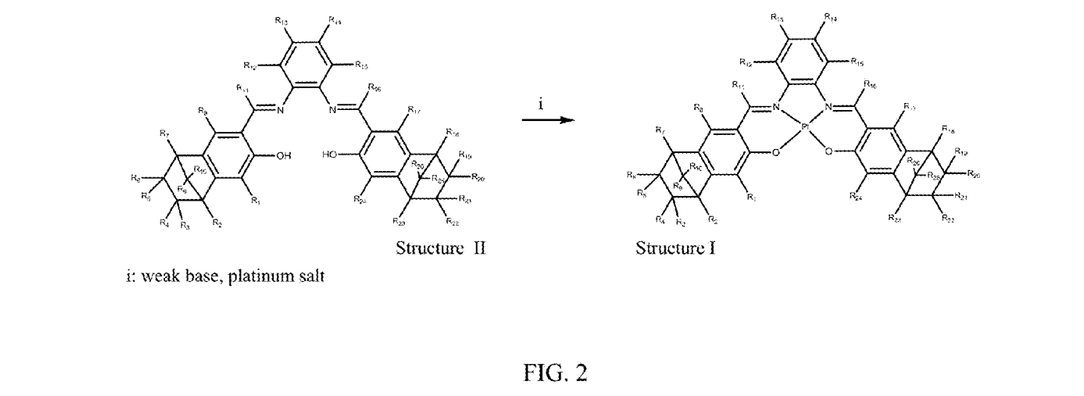
FIG. 2: a scheme for the synthesis of a complex having a chemical structure of structure I.
Figure 3:
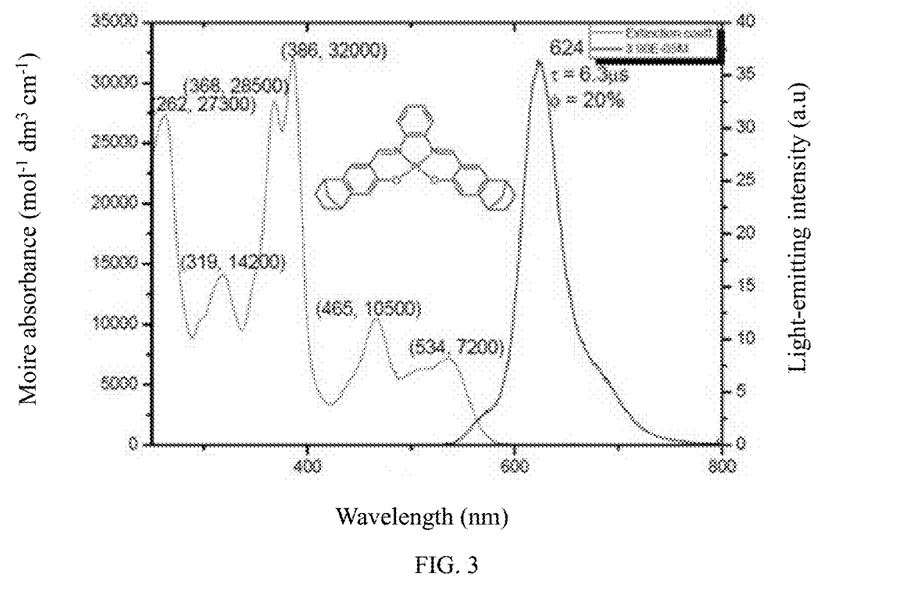
FIG. 3: Absorption and emission spectra of complex 101.
Figure 4:
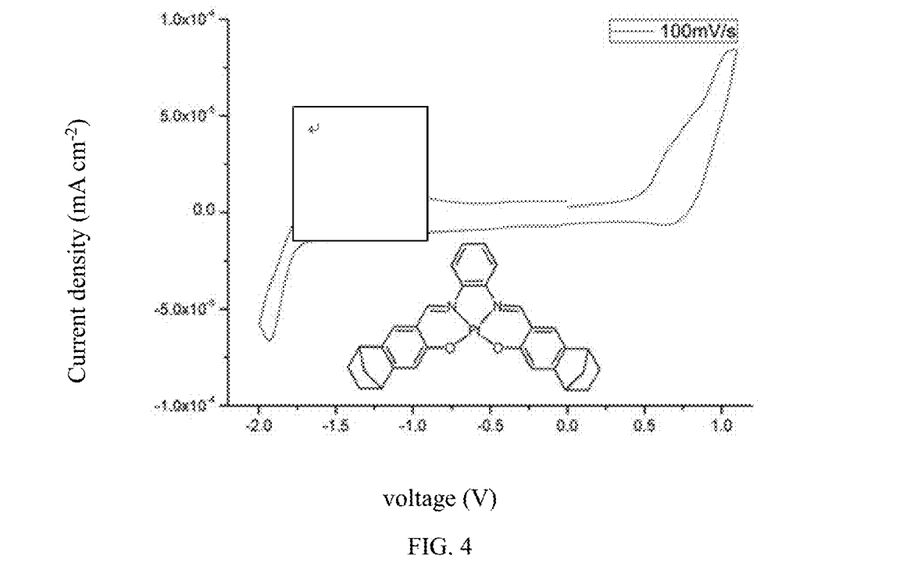
FIG. 4: Cyclic voltammetry of complex 101.
Figure 5:
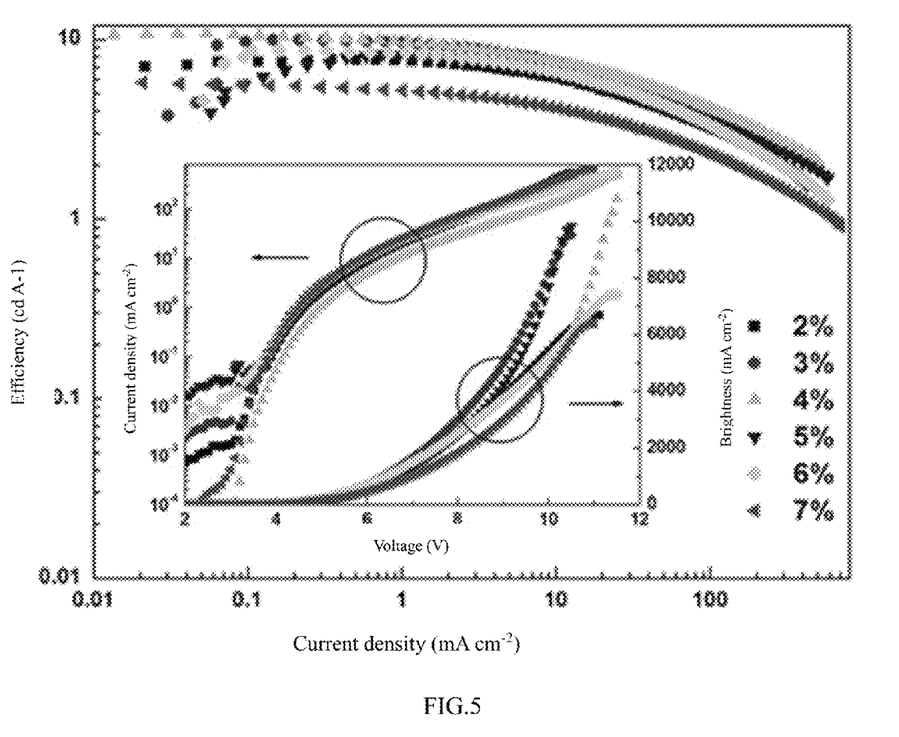
FIG. 5: Data of an OLED prepared with complex 101.
Figure 6:
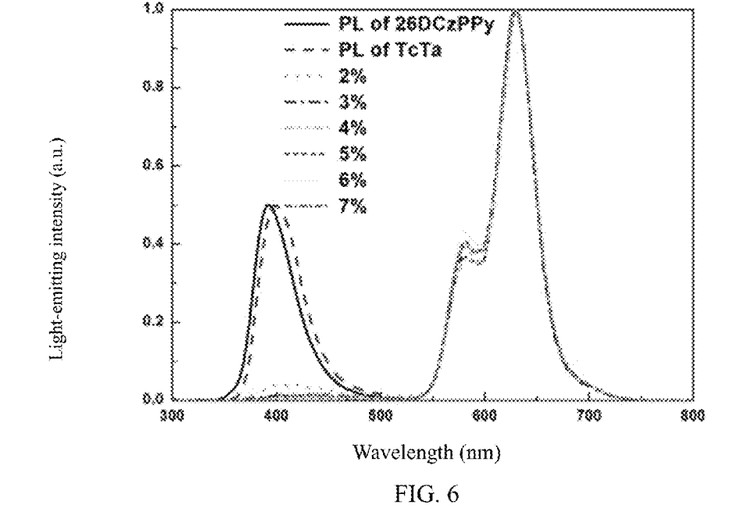
FIG. 6: Spectra of an OLED prepared with complex 101.

Embodiment 203—the General Method for Preparing a Complex Having the Structure I Referring to FIG. 2, firstly dissolve the ligand having the chemical structure of structure II (301) and twice of weak base in a small amount of hot dimethylformamide, then add platinum solution of methylsulfoxide, after reaction overnight, collect the precipitate by filtration, and then purify by recrystallization.

Embodiment 204—Preparation of Complex 101

Complex 101

Prepare complex 101 according to the method in the Embodiment 203, of which, the weak base is sodium acetate and the platinum salt is potassium tetrachloroplatinate, with a yield of 32%. $^1$H NMR (500 MHz, CD$_2$Cl$_2$) δ 8.76 (s, 2H), 7.97 (dd, J=6.0, 3.2 Hz, 2H), 7.32 (dd, J=6.1, 3.2 Hz, 2H), 7.28 (s, 2H), 7.08 (s, 2H), 3.36 (d, J=6.4 Hz, 4H), 1.97 (d, J=8.3 Hz, 4H), 1.80 (d, J=8.0 Hz, 2H), 1.62 (d, J=8.8 Hz, 2H), 1.31 (d, J=7.5 Hz, 4H).

Embodiment 205—Photophysical Properties of Complex 101

| $\lambda_{abs}$ [nm] ($\epsilon$[dm$^3$mol$^{-1}$cm$^{-1}$]) | $\lambda_{em}$ [nm] | τ [μs] | $k_q$ [10$^8$ dm$^3$mol$^{-1}$ s$^{-1}$] | $\Phi_{em}$ |
|---|---|---|---|---|
| 262 (27300), 319 (14200), 368 (28500), 386 (32000), 465 (10500), 534 (7200) | 624 | 6.3 | 0.1 | 0.20 |

Embodiment 206—Electrophysical Properties of Complex 10

| HOMO [eV] | LUMO [eV] | E$_g$ [eV] |
|---|---|---|
| −5.15 | −2.89 | 2.26 |

Embodiment 207—General Method for Preparing OLED by Thermal Dissociation

In a high vacuum environment (pressure <1×10$^{-6}$ torr), deposition is performed sequentially over the transparent material, the hole transporting layer, the electron-transporting layer, the anode and the metal cathode of the electron injection layer.

Embodiment 208 a device made according to Embodiment 207, wherein, the hole transporting layer is 4,4'-cyclohexylbis [N,N-bis(4-methylphenyl)aniline] (TAPC); The light-emitting layer consists of two distinct layers. The first layer is mainly a light-emitting layer of tris (4-carbazol-9-yl)-amine (TcTa) (host material) doped with a small amount of complex 101 (dopant), and the second layer is a light-emitting layer mainly composed of 9,9'-(2,6-pyridinediylbis-3,1-phenylene) bis-9H-carbazole (host material), doped with a small complex 101 (dopant); the electron-transporting layer is a 40 nm 3,3'-[5'-[3-(3-pyridyl) phenyl] [1,1':3',1"-terphenyl]-3, 3"-diyl]bipyridine (TmPYPB); and the electron injection layer is 1 nm lithium fluoride and the metal cathode is 100 nm aluminum.

Embodiment 209

Embodiment 209 illustrates the performance of OLED device using complex 101 as a light-emitting material according to the method described in Embodiment 208

| Doping ratio | V$_{turn-on}$ (V) | B$^{a)}$ (cdm$^{-2}$) | η$_{c\ max}$$^{b)}$ (cdA$^{-1}$) | η$_p$$^{c)}$ (lmW$^{-1}$) | η$_{c\ 1000}$(cdA$^{-1}$)$^{d)}$ (1000 cdm$^{-2}$) | η$_c$roll-off at 1000 cdm$^{-2}$ $^{e)}$ |
|---|---|---|---|---|---|---|
| 2% | 3.5 | 6712 | 7.75 | 6.35 | 5.28 | 32% |
| 3% | 3.5 | 9512 | 9.92 | 7.83 | 6.79 | 32% |
| 4% | 3.7 | 10810 | 10.82 | 9.00 | 7.02 | 35% |
| 5% | 3.5 | 9834 | 8.27 | 5.81 | 5.83 | 30% |
| 6% | 3.5 | 7424 | 8.72 | 7.20 | 5.90 | 32% |
| 7% | 3.5 | 6414 | 5.77 | 5.18 | 3.32 | 42% |

$^{a)}$maximum brightness;
$^{b)}$maximum current efficiency;
$^{c)}$maximum power supply efficiency;
$^{d)}$current efficiency at 1000 cdm$^{-2}$;
$^{e)}$efficiency attenuation = 1 − (η$_{c\ 1000}$/η$_{c\ max}$)

The invention claimed is:

1. A light-emitting material for light-emitting diode, wherein its structure is shown as formula I, (I)

Wherein, $R_1$-$R_{26}$ are independently hydrogen, halogen, hydroxy, unsubstituted alkyl, cycloalkyl, unsubstituted aryl, alkoxy, acyloxy, amino, nitro, acylamino, aralkyl, cyano, carboxyl, styryl, aminocarbonyl, carbamoyl, aryloxycarbonyl, phenoxycarbonyl or alkoxycarbonyl, and $R_1$-$R_{26}$ can independently form a 5- to 8-membered ring with other adjacent $R_1$-$R_{26}$ groups.

2. The light-emitting material according to claim 1, wherein $R_1$-$R_{26}$ are independently hydrogen, halogen, hydroxy, C1-C6 alkyl, five- or six-membered cycloalkyl, five- or six-membered aryl, alkoxy, amino, nitro, cyano, and carboxyl, and $R_1$-$R_{26}$ may independently form a five- or six-membered ring with other adjacent $R_1$-$R_{26}$ groups.

3. The light-emitting material according to claim 2, wherein $R_{3-8}$ and $R_{17-22}$ are independently hydrogen.

4. The light-emitting material according to claim 3, wherein $R_1$, $R_{11}$, $R_{16}$, $R_{24}$ are independently hydrogen, $R_2$, $R_{23}$, $R_{9-10}$, $R_{25-26}$ are independently hydrogen, $C_1$-$C_6$ are alkyl.

5. The light-emitting material according to claim 4, wherein $R_{12-15}$ are independently hydrogen, halogen, hydroxy, $C_1$-$C_6$ alkyl, 5-membered or 6-membered cycloalkyl, 5-membered or 6-membered aryl, amino, nitro, cyano, or 5-membered or 6-membered aromatic rings formed by $R_{13}$ and $R_{14}$.

6. The light-emitting material according to claim 5, wherein $R_{13}$ and $R_{14}$ are independently hydrogen, halogen, $C_1$-$C_4$ alkyl, amino, nitro, cyano, or a benzene ring formed by $R_{13}$ and $R_{14}$.

7. The light-emitting material according to claim 6, wherein $R_{12}$ and $R_{15}$ are independently hydrogen, $C_1$-$C_6$ alkyl.

8. The light-emitting material according to claim 7, wherein it is the compound having the following structures:

101

102

103

104

105

-continued

106

107

108

109

110

-continued

111

112

113

114

115

9. An organic light-emitting device containing one or more light-emitting materials for a light-emitting diode as described in claim 1.

10. The OLED according to claim 9, wherein the light-emitting material for light-emitting diodes is applied in layers in the device by thermal deposition; or the light-emitting material for light-emitting diodes is applied in layers in the device by spin coating; or the light-emitting material for light-emitting diodes is applied in layers in the device by ink jet printing.

* * * * *